United States Patent [19]
Esparza et al.

[11] Patent Number: 5,608,210
[45] Date of Patent: Mar. 4, 1997

[54] INFRARED AIDED METHOD AND APPARATUS FOR VENOUS EXAMINATION

[76] Inventors: Joel Esparza, 4930 National Ave., #7, San Jose, Calif. 95124; Ramendra D. Bahuguna, 825 Figwood Ct., San Jose, Calif. 95120; Gareth T. Williams, 15736 Izorah Way, Los Gatos, Calif. 95032

[21] Appl. No.: 618,744

[22] Filed: Mar. 20, 1996

Related U.S. Application Data

[63] Continuation-in-part of Ser. No. 315,128, Sep. 29, 1994, Pat. No. 5,519,208.
[51] Int. Cl.$^6$ ............................................ G01J 3/50
[52] U.S. Cl. .................. 250/226; 250/341.8; 128/664; 356/51
[58] Field of Search .................... 250/226, 330, 250/339.11, 339.14, 341.8, 559.44, 559.4, 559.41, 574; 128/664, 673, 692, 665, 634; 356/51

[56] References Cited

U.S. PATENT DOCUMENTS 3,893,447  7/1975  Hochheimer et al. ................. 356/51
4,817,622  4/1989  Pennypacker et al. ................ 128/664
5,086,229  2/1992  Rosenthal et al. ................. 250/339.12

*Primary Examiner*—Que T. Le
*Attorney, Agent, or Firm*—Robert S. Smith

[57] ABSTRACT

A device for aiding a technician to locate a vein for inserting a hyperdermic needle therein in which, in one embodiment, the technician dons a headpiece supporting an infrared light source illuminating an appropriate area of the flesh so that a view is generated showing the location of a subcutaneous vein. The headpiece also supports an infrared sensitive video camera and monitor screen in front of one eye and an opaque shield over the other eye. The lines of sight of the one eye viewing the screen is coincident with the line of sight of the camera and both lines of sight are directed toward the vein of the patient. The tip of the needle is moved into the line of sight then moved along the line of sight to the vein. In another embodiment, two cameras and screens are provided for viewing by both eyes and each camera and monitor can be positioned with line of sight coincident with the line of sight of the respective eye.

7 Claims, 5 Drawing Sheets

INFRARED AIDED METHOD AND APPARATUS FOR VENOUS EXAMINATION

CROSS REFERENCE TO EARLIER FILED APPLICATIONS

This application is a continuation-in-part of application Ser. No. 08/315,128 filed Sep. 29, 1994, now U.S. Pat. No. 5,519,208.

FIELD OF THE INVENTION

This invention relates to visual examination of the features of the human body such as the venous system and particularly to improvements in the method of gaining intravenous access by enhancing the view of the venous system by infrared illumination.

BACKGROUND AND INFORMATION DISCLOSURE

The difficulties of gaining intravenous access such as for drawing blood, intravenous fusion, etc., are well known to vary from one patient to another. Some patients have very prominent veins and this situation simplifies the procedure although, even for some of these patients, their veins have a tough resiliency that makes the veins difficult to penetrate with a hypodermic needle. In the context of this specification, the term, hypodermic needle, will be understood to mean any access device such as a syringe with needle for drawing blood, intravenous cathater, etc. In other patients, the veins are small, deepset, and scarcely visible so that gaining intravenous access is very unpleasant for both the practitioner and the patient. The complexion of the patient can be another troublesome factor. For example, the veins of Afro-Americans are not nearly as visible as the veins of many other patients which hinders the process of finding a vein and drawing blood therefrom. Infants have immature vascular development. Obese patients have venous structure that is difficult to penetrate. At the very least, these complications can greatly increase the stress experienced by the patient. At worst, delays in gaining intravenous access can result in death.

U.S. Pat. No. 4,817,612 to Pennypacker et al discloses an arrangement shown in FIGS. 1 and 2 (prior art) for locating vascular structures V including a conventional video display D having a monitor screen M, viewed by the eye of an observer through a lens system 14. A mirror 16 deflects an image through filter F to camera C which includes a charged coupled device 20 with lens system 22. A problem with the arrangement of FIGS. 1 and 2 is that the device must be supported by placing the bottom edge of the mirror 16 against the surface of the limb of the patient. This is not an acceptable practice for many situations. A second problem is that palcement of the mirror 16 in the vicinity of the patient interferes with applying the hypodermic needle to the required location on the patient. A third consideration is a limited range of location for placement of the light L of the Pennypacker system. A fourth considation is the requirement that the patient remain motionless for an extended period of time in one location which is a difficult requirement for small children. A fifth consideration is that the cost of the Pennypacker device, including the half silvered mirror and optical system for reflecting an image of the area of interest onto the camera is greater than the cost of the present invention.

THE INVENTION

OBJECTS

It is an object of this invention to provide a method and apparatus for gaining intravenous access from a patient that is less stressful than the method of the present state of the art. In pursuing this objective, it is recognized that some patients have veins that are not prominent or otherwise difficult to locate and the method of this invention facilitates locating these veins. It is a further object of this invention that, once an attendant locates the vein, he may then position the tip of a hyperdermic needle close to the point of entry with improved accuracy and therefore decreased trauma experienced by the patient.

SUMMARY

This invention is directed toward a method for aiding a user to insert a hypodermic needle into the vein of a patient. The area of the patient containing the vein is illuminated by infrared light so that the veins are clearly delineated. An infrared sensitive video camera presents a view of the area on a monitor directly in front of the eye of the user wherein the line of sight of the camera coincides with the line of sight of the user. The user is thereby enabled to guide the tip of a hypodermic needle proximal to the site of the vein by moving the needle point along his line of sight toward.

The human proprioperceptive system is conditioned to place a first point (e.g., the tip of a hypodermic needle) exactly onto a second point (e.g., a location on a vein) using either one of two modes.

In one mode, sight of one eye is blocked off. The viewer looks with one eye at the second point (vein) to establish a line of sight, moves the first point (needle) into intersection with the line of sight and then moves the first point along the line of sight until it comes into coincidence with the second point. This mode is illustrated by the well known example of a hunter, closing one eye and establishing the line of sight of the second eye by squinting along the "sight" at the end of the barrel to the target.

In another mode by which a first point is brought into coincidence with a second point, each eye views the second point along its own line of sight and stereo-optically combines the two images (each image formed by one and only one eye) to provide the sensation of three dimensions. In response to this sensation, the brain is conditioned to manually move the first and second points into coincidence. This second mode has the advantage of presenting the view in three dimensions but the disadvantage that it is only effective when the two points are close to the observer.

In one embodiment of the invention which is practiced using the first mode, the apparatus includes a lamp, a charge coupled video camera and a viewing screen all supported by a headpiece on the head of a user. The lamp is arranged to illuminate a surface area of the patient with radiation having a selected wavelength that is reflected by all of the surface area except where veins are located. The viewing screen is viewed by only one eye of the user and the other eye of the user is shielded by a blank dark screen. A charge coupled video camera is mounted on the headpiece directly in front of the single viewing screen which is in front of one eye such that the line of sight of the camera is coincident with the line of sight of the eye viewing the viewing screen. The venous system viewed on the viewing screen appears as dark lines that clearly stand out. Because the line of sight of the camera is coincident with the line of sight of the users eye, the user is able to position the tip of the hypodermic needle on his line of sight and move the tip of the needle along his line of sight into contact with a location on the patients body where veins are observed. The user is thereby enabled to locate the hypodermic needle at the appropriate point of entry into the vein.

In another embodiment, practiced according to the second mode, a headpiece supports a pair of infrared sensitive camera and monitor screen. Each screen is directly in front of an eye and the line of sight of each camera is aligned with an eye. Each screen and its camera is rotably mounted so that the orientation of the screen can be adjusted according to the distance between the eyes and the vein of the patient. A light source projecting an infrared beam is rotatabley mounted for illumuinating the area of flesh containing the subcutaneous vein.

An LED located on the needle about ¼ inch from the tip and emitting light having wavelength readily discernible through the projection system of the apparatus is a further aid to maintaining registration between the tip and point of entry.

DESCRIPTION OF A PREFERRED MODE

Figure 1:
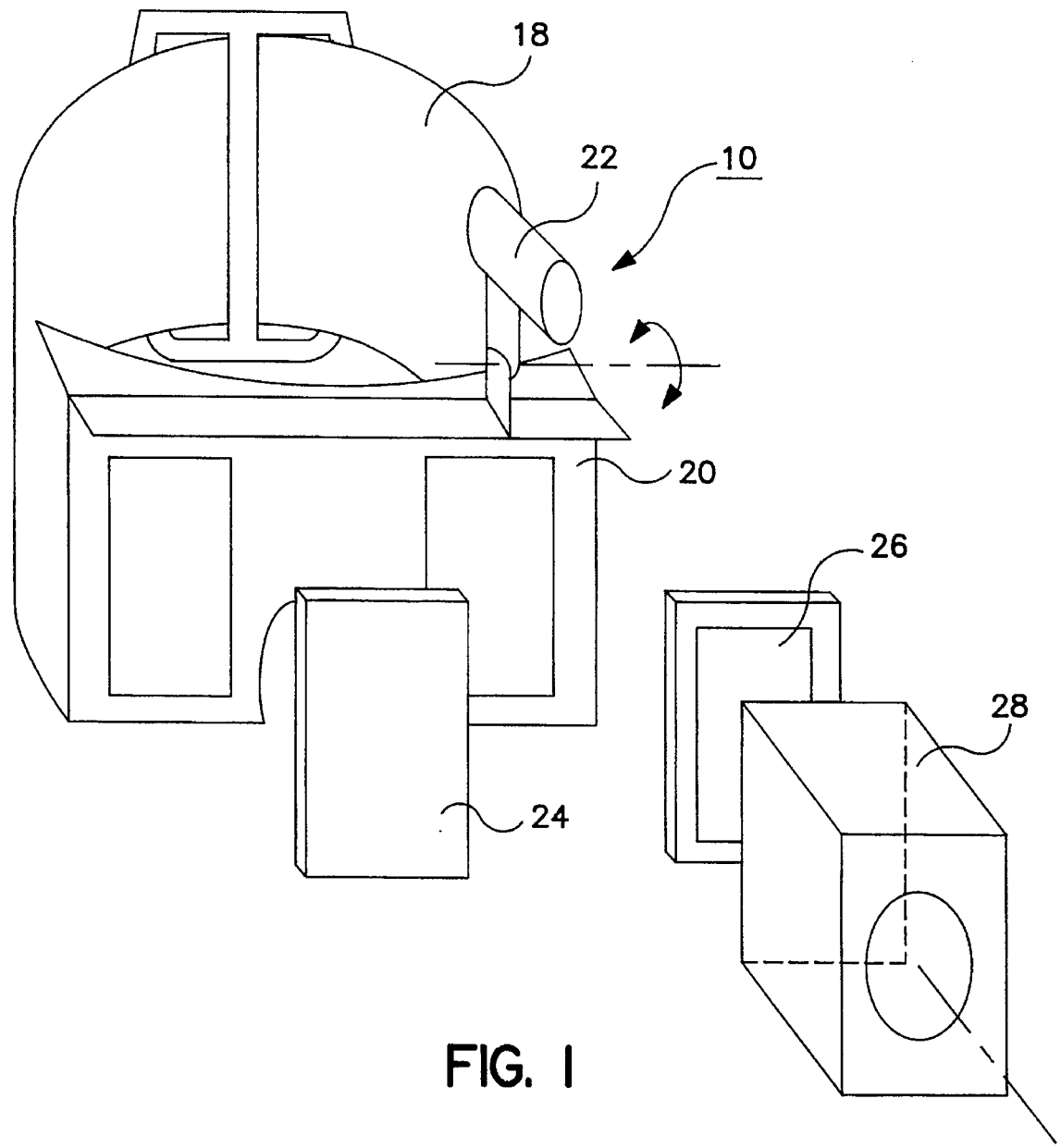
FIG. 1 shows an exploded view of an embodiment of this invention for using one eye utilizing one line of sight.
Figure 2:
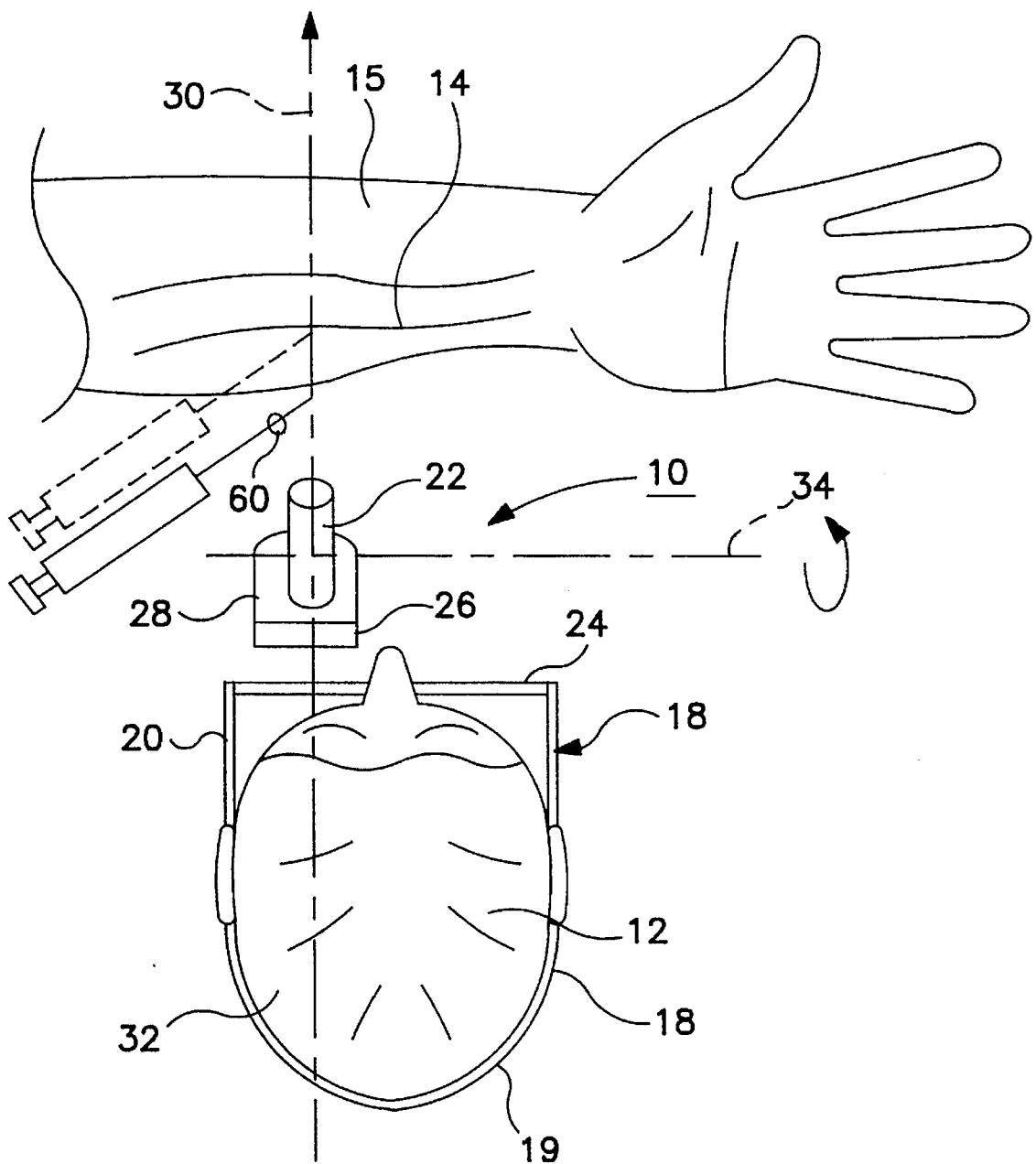
FIG. 2 is an assembly view of the embodiment of FIG. 1.

Turning now to a discussion of the figures, FIG. 1 is an exploded view showing an embodiment of a vascular viewer 10 of this invention. FIG. 2 is a top view showing the user 12 viewing the vein 14 of a patient through the vascular viewer 10 mounted on the head 12 of the user.

The viewer 10 includes a headpiece 19 having an adjustable band 18 and a frame 20 which supports:

an infrared light source 22;

an opaque screen 24 which shields the vision of one eye;

a video monitor screen 26 positioned directly in front of the other eye;

an infrared charge coupled video camera 28.

As shown in FIG. 2, one eye is blocked and the monitor screen 26 and video camera 28 are placed directly in front of the other eye such that the line of sight 30 of the camera 28 coincides with the line of sight 32 of the eye viewing the monitor screen 26.

The light source 22 projects an infrared light beam onto an area of flesh 15 to be examined for veins 14. The light beam contains a range of infrared wavelengths which are substantially absorbed by subcutaneous veins and reflected by vein-free areas of the flesh thereby generating a view of the flesh showing the veins.

The video camera 28, being sensitive to the infrared wavelengths of the light source 22, generates a video signal of the view of the flesh showing the veins.

The light source 22 is mounted to permit rotating the beam about an axis of rotation 34 that is perpendicular to the line of sight 30 of the video camera 28 so that the user can select a rotational setting of the light where the light beam intersects the line of sight of the video camera at a location whose distance from the viewing screen is convenient for the user.

Figure 3:
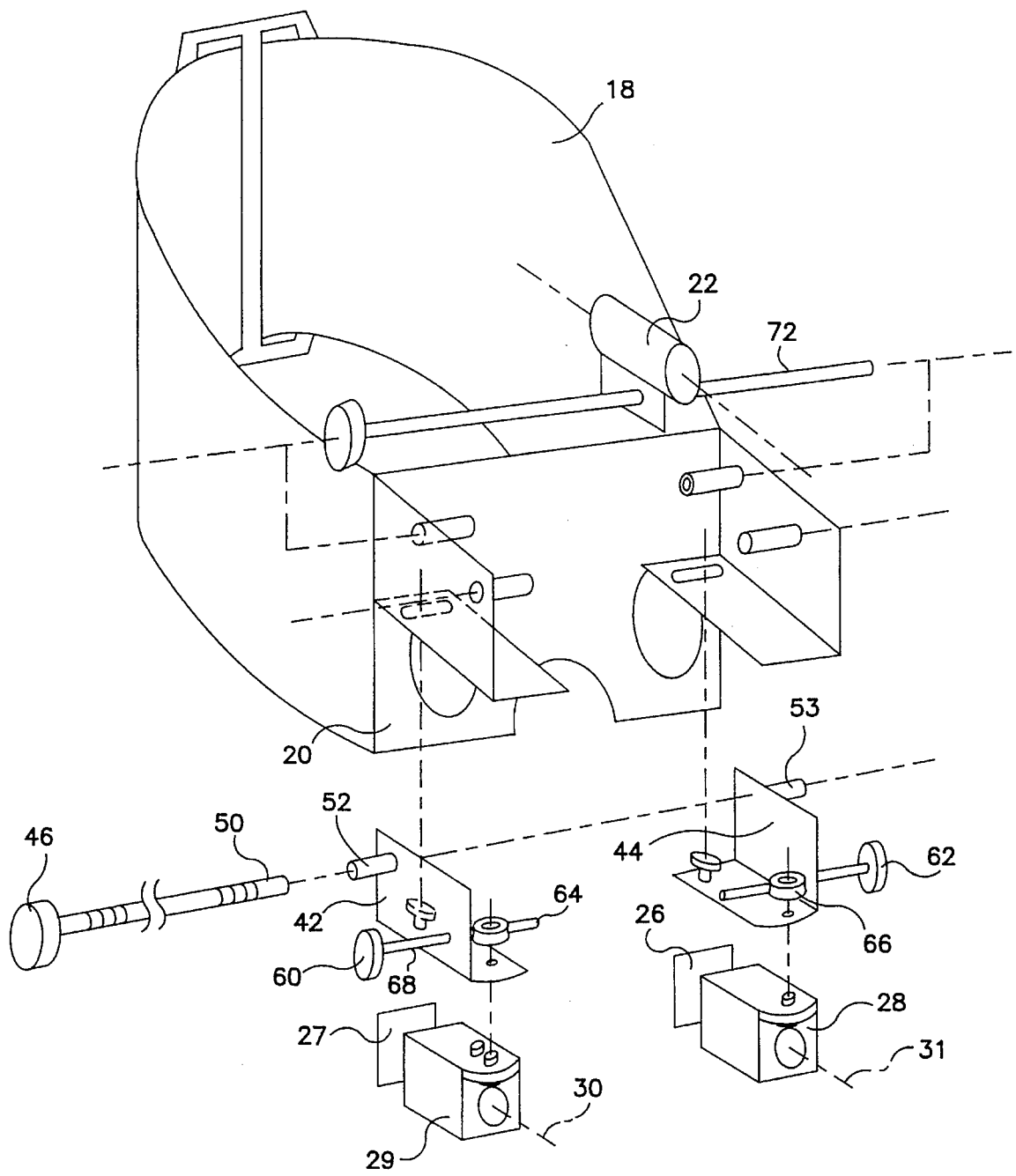
FIG. 3 shows an exploded view of a second embodiment of this invention.
Figure 4:
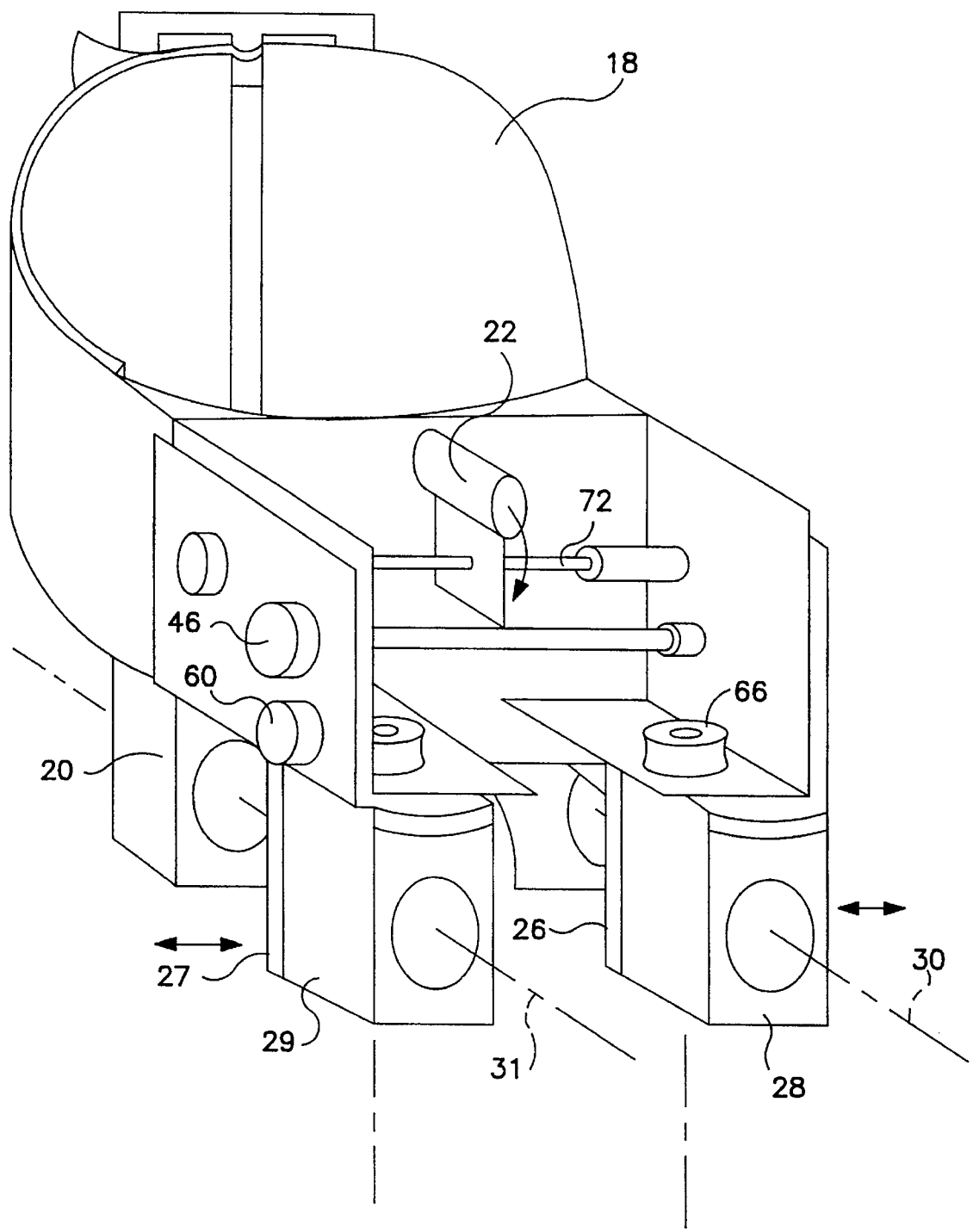
FIG. 4 shows an assembly view of the embodiment of FIG. 3.

FIG. 3 is an exploded view and FIG. 4 is an assembly view of another embodiment of the invention which is based on the second mode by which the user positions a the tip of the hypodermic needle onto a vein. According to this embodiment, the headpiece supports a pair of video cameras, 28 and 29, each camera in front of an eye respectively. Cameras 28 and 29 am rotatably mounted onto brackets 42, and 44. Orientation of the cameras 28 and 29 can be adjusted by turning knobs 60 and 62 mounted on shafts 68 and 70 that engage worm gears 64 and 66 mounted on cameras 28 and 29 respectively. Brackets 42 and 44 are supported on frame 20 to move toward or away from one another by turning knob 46. This is achieved by knob 46 being mounted on shaft 50 which is threaded into collar 52 with a right hand thread and into collar 53 by a left hand thread. By adjusting the orientation and separation from each other of cameras 28 and 29, the line of sight 30 and 31 of cameras 28 and 29 can be made coincident with the line of sight of the respective eye of the viewer viewing a respective monitor screen, 26 and 27. Light source 22 is rotably mounted on shaft 72 which is journalled into frame 20 to rotate such as to illuminate the location (vein) where the lines of sight of cameras 28 and 29 intersect one another.

These two embodiments overcome the problem of simply viewing a monitor showing a cutaneous vein viewed by a camera wherein the line of sight of the camera is not coincident with the line of sight of the viewer. The problem arises because the viewer's proprioceptive reflexes are not conditioned to move accurately and instinctively along the line of sight of the camera when the lines of sight of the eye and camera are not coincident.

The two embodiments also enable the viewer to follow motion of the patient's arm and avoid contact of the patient's arm with the instrument in contrast to the device of the prior art. This is a very important requirement especially in attempting to withdraw blood from a child.

As a further aid in the practice of this invention, a small LED 66 (FIG. 2) emitting light in the near infrared wavelength range, is located near the tip of the hypodermic needle and can thereby be seen by the viewer as he positions the tip needle at the insertion point.

Figure 5:
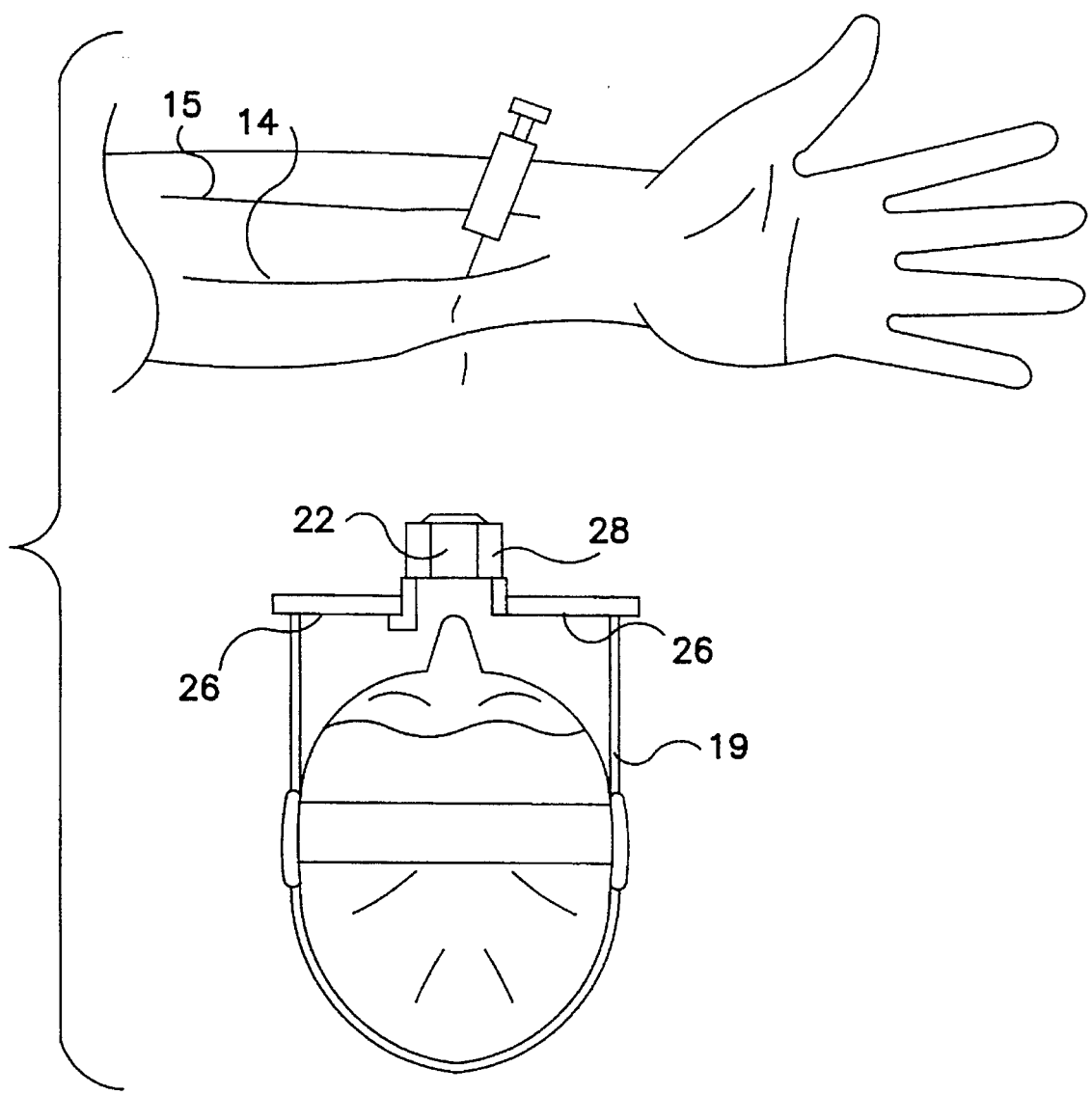
FIG. 5 shows another embodiment utilizing two screens.

FIG. 5 shows another arrangement of a head mounted television monitor and viewing screen for aidong venous injection which is based on a characteristic of human visual perception according to which, when an object is being very viewed that is very close to the face of the observer, each eye of the observer sees the object from a different perspective and therefore each eye forms an image that is different from the image formed by the other eye. Under this condition, one eye will dominate and the brain will ignore (tend to bock out the image from the nondomiant eye. According to the arrangement shown in FIG. 5, a small video camera 28, light source 22 and a pair of monitor screens 26 are supported on the head piece 19. The camera 28 is positioned between the eyes of the observer and one screen is positioned directly in front of one eye and the other screen is positioned directly in front of the other eye. The view recorded by the camera is identical for both eyes.

Other variations of this invention may be considered which are within the scope of this invention. We therefore wish to define our invention by the appended claims.

What is claimed is:

1. An apparatus for aiding a user injecting the tip of a hypodermic needle into a subcutaneous vein in the flesh of a patient, said apparatus comprising:

light source means for providing an infrared light beam such that, when said light beam is directed onto said flesh, one portion of said light beam is incident on a first area of flesh containing said vein and another portion of said light beam is incident on a second area of flesh that is vein free;

said light beam containing a range of wavelengths selected such that said one portion of said light beam is substantially absorbed by said first area containing said vein and said second portion of said light beam is substantially reflected by said second area that is vein free whereby a view of said subcutaneous vein in said flesh is created;

a first video camera having a response to said wavelengths and a line of sight such that when said line of sight of said first video camera is directed toward said view, a video signal representing said view is developed by said first video camera;

a first monitor means having a first screen and connected to said first video camera for receiving said video signal from said first video camera and presenting on said first screen an image of said view generated from said video signal;

head support means for supporting said light source means, said first video camera and said first monitor means on the head of a user adapted such that said light beam intersects said line of sight of said first video camera and said line of sight of said first video camera is coincident with a line of sight of one eye of said user when said one eye of said user is viewing said image on said first screen whereby said user wearing said head support means is enabled to position his/her head such that said first and second areas of flesh are located at a position where said line of sight of said first video camera intersects said light beam and said user is enabled to move said tip of said hypodermic needle into said line of sight of said first video camera and move said tip toward said second area of flesh preparatory to inserting said tip into said vein.

2. The apparatus of claim 1 which further comprises a second video camera having a response to said wavelengths and a line of sight such that when said line of sight of said second video camera is directed toward said first and second areas of said flesh, a video signal representing a view of said first and second areas is developed by said second video camera;

a second monitor means having a second screen and connected to said second video camera for receiving said video signal developed by said second video camera and presenting on said screen of said second monitor an image of said view generated from said video signal developed by said second video camera;

said head support means supporting said second video camera and said second monitor means adapted such that a line of sight of said second video camera inersects said line of sight of said first video camera and said line of sight of said second video camera is coincident with a line of sight of another eye of said user when said another eye of said user is viewing said image on said second screen whereby said user wearing said head support means is enabled to locate his/her head such that said first and second areas of flesh are located at a position where said lines of sight of said first and second video cameras intersect one another and intersect said light beam whereby said user has an impression of three dimensions of said view when said first and second ares of flesh are located at said position.

3. The apparatus of claim 2 which further comprises means for selecting an angle of intersection between said lines of sight of said first and second video cameras according to convenience of said user.

4. The apparatus of claim 3 which further comprises means for changing an angle of intersection between said light beam and lines of sight of said first and second video cameras such that distance from said position to said user is selectable according to the user's convenience.

5. The apparatus of claim 1 which further comprises an opaque patch supported by said head support means and adapted for being positioned over another eye of said user whereby said user is further enabled to move said tip of said hypodermic needle into said line of sight of said first video camera and move said tip toward said second area of flesh preparatory to inserting said tip into said vein.

6. A method for injecting the tip of a hypodermic needle into a subcutaneous vein in the flesh of a patient, said method comprising the steps of:

(a) providing an apparatus comprising:

(i) light source means for providing an infrared light beam such that, when said light beam is directed onto said flesh, one portion of said light beam is incident on a first area of flesh containing said vein and another portion of said light beam is incident on a second area of flesh that is vein free;

(ii) said light beam containing a range of wavelengths selected such that said one portion of said light beam is substantially absorbed by said first area containing said vein and said second portion of said light beam is substantially reflected by said second area that is vein free whereby a view of said subcutaneous vein in said flesh is created;

(iii) a first video camera having a response to said wavelengths and a line of sight such that when said line of sight of said first video camera is directed toward said view, a video signal representing said view is developed by said first video camera;

(iv) a first monitor means having a first screen and connected to said first video camera for receiving said video signal from said first video camera and presenting on said first screen an image of said view generated from said video signal;

(v) head support means for supporting said light source means, said first video camera and said first monitor means on the head of a user adapted such that said light beam inersects said line of sight of said first video camera and said line of sight of said first video camera is coincident with a line of sight of one eye of said user when said one eye of said user is viewing said image on said first screen;

(b) positioning the head support means on the head of a user;

(c) positioning the head such that said first and second areas of flesh are located at a position where said line of sight of said first video camera intersects said light beam;

(d) moving said tip of said hypodermic needle into said line of sight of said first video camera and moving said tip toward said second area of flesh preparatory to inserting said tip into said vein;

(e) inserting said tip into said vein.

7. An apparatus for aiding a user injecting the tip of a hypodermic needle into a subcutaneous vein in the flesh of a patient, said apparatus comprising:

light source means for providing an infrared light beam such that, when said light beam is directed onto said flesh, one portion of said light beam is incident on a first area of flesh containing said vein and another portion of said light beam is incident on a second area of flesh that is vein free;

said light beam containing a range of wavelengths selected such that said one portion of said light beam is substantially absorbed by said first area containing said vein and said second portion of said light beam is substantially reflected by said second area that is vein free whereby a view of said subcutaneous vein in said flesh is created;

a video camera having a response to said wavelengths and a line of sight such that when said line of sight of said video camera is directed toward said view, a video signal representing said view is developed by said video camera;

a first monitor means having a first screen and connected to said video camera for receiving said video signal from said video camera and presenting on said first screen an image of said view generated from said video signal;

a second monitor means having a second screen and connected to said video camera for receiving said video signal from said video camera and presenting on said second screen an image of said view generated from said video signal;

head support means for supporting said light source means, said video camera, said first monitor means having a first screen and said second monitor means having a second screen on the head of a user adapted such that said video camera is postioned between eyes of said user and directed toward a view directly in front of a face of said user and said first screen is positioned directly in front of one eye of said user and said second screen is positioned directly in front of another eye of said user.

* * * * *

UNITED STATES PATENT AND TRADEMARK OFFICE
CERTIFICATE OF CORRECTION

PATENT NO. : 5,608,210
DATED : March 4, 1997
INVENTOR(S) : Esparza, Joel; Bahuguna, Ramendra D. and Williams, Gareth T.

It is certified that error appears in the above-identified patent and that said Letters Patent is hereby corrected as shown below:

Column 5,
Line 42, delete "second" and insert -- first --.

Column 6,
Lines 21 and 66, delete "second" and insert -- first --.

Signed and Sealed this

Twenty-first Day of February, 2006

JON W. DUDAS
*Director of the United States Patent and Trademark Office*